United States Patent [19]

Schneidmiller

[11] Patent Number: 4,638,592
[45] Date of Patent: Jan. 27, 1987

[54] FLY TRAP AND ATTRACTANT THEREFORE

[76] Inventor: Rodney G. Schneidmiller, E. 8604 S. Riverway, Spokane, Wash. 99206

[21] Appl. No.: 789,850

[22] Filed: Oct. 21, 1985

[51] Int. Cl.⁴ ............................................. A01M 1/10
[52] U.S. Cl. .......................................... 43/122; 426/1
[58] Field of Search ............................... 43/122; 426/1

[56] References Cited

U.S. PATENT DOCUMENTS

| | | | |
|---|---|---|---|
| 1,566,619 | 12/1925 | Schlossareck | 43/122 |
| 3,820,273 | 6/1974 | Novak | 43/122 X |
| 3,846,557 | 11/1974 | Mulla et al. | 426/1 |
| 3,863,384 | 2/1975 | Weatherston et al. | 43/114 |
| 3,885,341 | 5/1975 | Kuchenbecker et al. | 43/121 X |
| 4,360,987 | 11/1982 | Lowder | 43/122 |
| 4,501,088 | 2/1985 | Boisvert et al. | 43/122 X |

FOREIGN PATENT DOCUMENTS 38295 2/1915 Sweden ............................... 43/122

Primary Examiner—Kuang Y. Lin
Assistant Examiner—Carmine Cuda
Attorney, Agent, or Firm—Keith S. Bergman

[57] ABSTRACT

A containment type fly trap providing a translucent container releasably carrying an opaque yellow-green to yellow top with structure to aid hanging support. The top is upwardly convex and defines plural downwardly extending indentations each carrying in its medial part a conical entry tube with a sharp edge defining its lower orifice, above the top of the container structure. An aqueous odoriferous mixture comprising yeast, egg and milk in a fermenting state is carried in the container as an attractant and to aid the demise of entrapped flies.

7 Claims, 3 Drawing Figures

FLY TRAP AND ATTRACTANT THEREFORE

BACKGROUND OF INVENTION

1. Related Applications

There are no applications related hereto now filed in this or any foreign country.

2. Field of Invention

My invention relates generally to containment type insect traps and more particularly to such a trap for flies and an aqueous odoriferous attractant to be carried therein.

3. Description of Prior Art

Flies have long been a noxious pest and a danger to mankind and his property. By reason of this, many and various traps to remove the insects from the environs of humans have heretofore become known. The instant invention adds a new member to this class of device that entraps flies to aid their demise or containment for future disposition.

Fly traps heretofore known have apparently not been particularly concerned with the instinctive reaction or so called "psychology" of flies. Because of this the nature and combinations of their structures have been somewhat haphazard and oftentimes have not provided a means of maximum efficiency for catching flies, if in fact they even have been practical for this purpose. Because of this, and with the advent of better chemical pesticides, most flies in the recent past have been controlled and destroyed largely by pesticides. Many pesticides have become known and most quite effectively fulfill their purpose.

Many of these chemical pesticides, however, deleteriously affect the environment generally and oftentimes even human physiology. Because of this pesticides have been stringently controlled and many of the more effective pesticides have been banned entirely from general use. The fly population however remains, the need for its control becomes even greater, and again the fly trap is becoming a practical and desired means for controlling fly populations.

The instant invention provides a fly trap created in consideration of fly instinct to provide a containment type device of maximum efficiency with each of its individual elements created to accommodate particular desires and characteristics of flies and all of such elements effectively combined in a symbionic relationship that enhances their individual features. It is distinguished from the prior art at least in the aspects following.

My trap provides a translucent containment chamber covered in its upper part by an opaque cap defining entrance orifices extending downwardly into the containment chamber. The cap is colored in the range of yellow-green to yellow as this color range provides an optical attractant for flies. Entryways provide indented transition elements communicating with downwardly and inwardly extending entry tubes to accommodate a fly's normal motion pattern of approaching an object from above when in flight and moving in a downward direction when crawling. The opaque material from which the entrance orifices are formed further enhances the probability of fly entry into the entrapment chamber, because that chamber is formed of translucent material and will allow the passage of light therein to appear brighter to an entering fly then the passageway through which entrance is gained, since that passageway is formed of opaque material. This enhances the fly's general instinct of moving toward a light source or light area. The dimpled transition surface surrounding an entry tunnel accentuates and aids this activity by directing a fly in the right direction. Many prior art devices have provided some sort of bottom-type entry for insect traps and though such an entry accommodates the instinctual behavior of some insects, and particularly wasps and yellow jackets, it is adverse to the instinctual behavior of flies and is much less efficient in trapping flies than are the entryways of my device.

The efficiency of entryways in entrapping flies in containment type fly traps increases proportionately with the increase of angle of the access channel of the entryway from the horizontal, though few prior art fly traps, if any, have recognized this principle except possibly by accident. The entryways to the entrapment chamber of my trap provide truncated conics having smooth surfaces defining their lower orifices orientated at an acute angle to each other so that the lower orifice has a sharp edge. This structure increases the probability of a fly's remaining in the entrapment chamber once it gets there, because of fly instinct that is adverse to crawling over a sharp edge, no matter how that edge may be oriented. The structure further enhances this action because the orifice size limits the physical ability of the fly to move upwardly through an entry orifice with spread wings and the smooth, substantially vertical surfaces do not allow the insect to gain a foothold about the orifice to allow it to crawl over the lowermost edge in the first instance, even if it so desired.

The translucent nature of the structure defining the containment chamber also enhances the demise of flies within that chamber. The trap is designed primarily for outdoor use and when heat waves enter the containment chamber, they tend to reflect and refract from the inner surfaces defining that chamber to remain therein to create what is commonly known as the "greenhouse effect" which tends ultimately to raise the temperature in the containment chamber. The raised temperature enhances fly activity, stimulates fright and enhances escape excitement, all to more rapidly exhaust an entrapped fly and hasten its ultimate demise within the entrapment chamber. The translucent or transparent nature of the container also tends to enhance the attractive action of my trap as flies tend to be attracted to an area where other flies congregate, even though they are not a particularly social insect. This reaction apparently results by reason of a fly's associating the congregation of his brethern with presence of a food source and its desire to find that food source for its own imbibition.

An aqueous based attractant containing egg, milk and yeast in active fermentation is contained in the entrapment chamber. The mixture may contain bicarbonate of soda in warmer climates to retard fermentation for prolonged life of the attractant mixture. The odoriferous products of this fermentation reaction are especially attractive to flies and somewhat selectively so. Since the ordoriferous attractants from the fermentation process are generally heavier than the surrounding air, they tend to settle in and diffuse from trap entryways so that they are most concentrated in an entryway and form a bulbous concentration thereabout with a concentration gradient varying somewhat in ratio to distance from the entryway. With this form of attractant dispersement, flies instinctively proceed toward the greater concentration of the attractant, which is associated with proximity to a food source, and therefore to and through the entryways leading to the entrapment chamber. This particular attractant seems quite selective to flies and generally not too attractive to other insects. It provides a substantially higher probability of fly entrapment than entrapment of other types of insects, especially bees, which most probably are not desired to be entrapped.

The attractant serves a further purpose in aiding the demise of flies within the entrapment chamber. As flies become exhausted, they generally cease flying or move downwardly by reason of gravity or otherwise, become wetted and eventually drown in the attractant medium. The yeast may also produce carbon dioxide as a product of its metabolism and if so, this reduces oxygen content in the entrapment chamber and tends to aid asphyxiation of flies therein. This action further enhances the attractant as the fly bodies therein tend to putrefy in the aqueous attractant medium and this reaction seems to enhance the olfactory attracting potentially of the medium. The attractant is such that it may readily be admixed from components obtained by a user or might be readily supplied in dry form to be mixed with water at the time of use by a user. The attractant contains only simple ingredients which are generally not dangerous to humans or other animals and contains no poisonous substances as such.

The olfactory attractants for flies are generally noxious to humans and domestic animals to increase the probability that neither humans nor animals, no matter how unsophisticated, will become involved with the attractant.

Various of the individual features of my trap and attractant have become known heretofore, either deliberately or accidentally. My invention therefore resides not in any one of these individual features per se, but rather in the synergistic combination of all of them in the particular structure set forth to accomplish the functions necessarily flowing therefrom.

SUMMARY OF INVENTION

My invention generally provides an entrapment chamber defined by a light translucent peripheral element releasably carrying an opaque cylindrical top defining entryways.

The top is formed of bright yellow-green optically opaque material and is configured with a convex upper surface with an outstanding bracket in its medial portion to aid a hanging-type support. The cap defines a plurality of spacedly arrayed concave entryway dimples serving as a transition element between the top and downardly extending entry channels that terminate in the upper portion of the entrapment chamber. The entry tunnels are defined by truncated conics with lowermost apices and lower orifices defined by acutely sharp edges.

The trap carries an aqueous attractant including egg, milk and yeast which in the environs of the trap will actively ferment. Sodium bicarbonate may be added to prolong attractant life. The trap is normally placed in an outdoor environment where it receives some light and warmth.

In creating such a fly trap, it is:

A principal object of my invention to create a simple containment structure of inexpensive manufacture that yet maximizes fly entrapment by recognizing the instincts of flies and applying them to the design of trap elements to maximize entrapment potentiality.

It is a further object of my invention to provide such a trap that has a bright yellow-green to yellow top entry portion that serves as an optical attractant to flies.

A further object of my invention to provide such a trap that has an upper positioned entry area that provides entry by normally downwardly directed flight approach and subsequent downward crawling motion of a fly.

A further object of my invention to provide such a trap that defines entryways in an opaque top portion with a translucent entrapment chamber therebelow to provide greater light below entryways than therein to attract flies to enter through the entryways.

A further object of my invention to provide such a trap that carries a liquid attractant including yeast, egg and milk in an aqueous solution for active fermentation, which may be retarded by sodium bicarbonate if necessary, to present an olfactory attractant for flies.

A further object of my invention to create such a trap that passes the olfactory attractant through the entryways to a trap's environ so that attractant odor will be greatest at the entryway to increase the probability of attracting flies to that position.

A further object of my invention to provide such a trap that enhances the demise of flies by the greenhouse effect in the entrapment chamber, lack of oxygen therein and the presence of aqueous media in the lower portion thereof.

A still further object of my invention to provide such a trap that is of new and novel design, of rugged and durable nature, of simple and economic manufacture and one otherwise well suited to the uses and purposes for which it is intended.

Other and further objects of my invention will appear from the following specification and accompanying drawings which form a part hereof. In carrying out the objects of my invention, however, it is to be understood that its essential features are susceptible of change in design and structural arrangement with only one preferred and practical embodiment being illustrated in the accompanying drawings as is required.

BRIEF DESCRIPTION OF DRAWINGS

In the accompanying drawings which form a part hereof and wherein like number of reference refer to similar parts throughout.

DESCRIPTION OF THE PREFERRED EMBODIMENT

Figure 1:
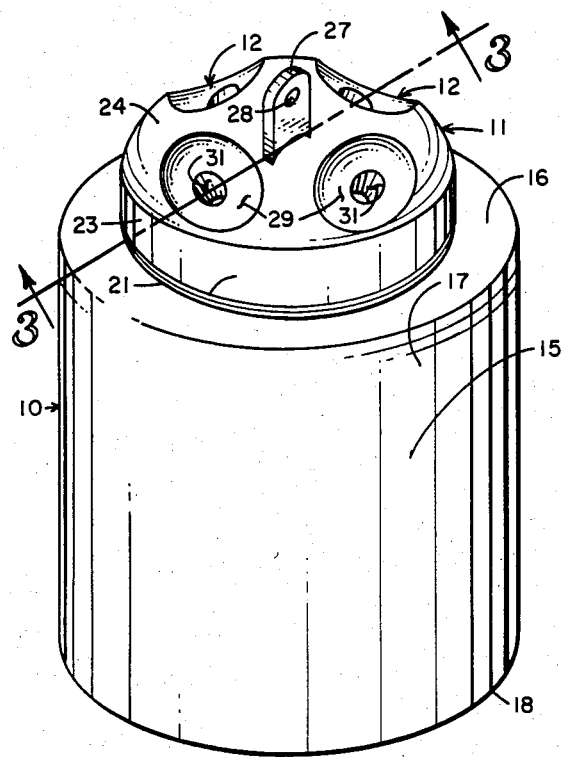
FIG. 1 is an isometric surface view of my invention showing its various parts, their configuration and relationship.
Figure 2:
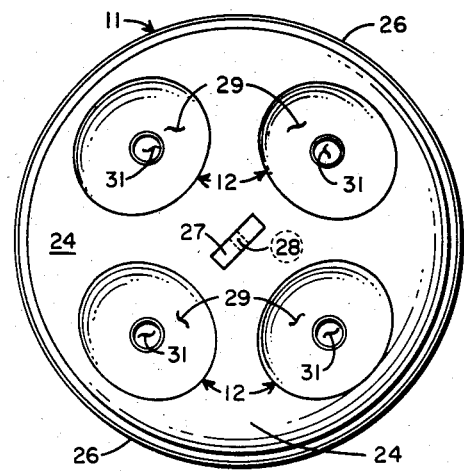
FIG. 2 is an orthographic top or plan view of the top member of the fly trap shown in FIG. 1.

Referring now to the drawings in more detail, it will be seen that my invention provides peripheral body 10 defining a neck that releasably carries top 11 which defines plural entry structures 12. The chamber defined by trap body 10 contains aqueous attractant 13.

Body 10 is a cylindrical container formed by structurally interconnected bottom 14, vertical side 15 and top annulus 16 in its upper part. Preferably the adjoining edges 17 of these elements are rounded to provide a more curvilinear structure with greater strength and rigidity, especially if the structure be formed of polymeric material. Bottom 14 preferably provides depending foot annulus 18, immediately inwardly adjacent its periphery, to aid in supporting the device on a flat surface and again to provide additional structural rigidity and strength, especially in the area of the joinder of bottom and vertical cylindrical side 15.

The inner portion of top annulus 16 structurally interconnects cylindrical neck 19 extending upwardly a spaced distance thereabove. Neck 19 again has curvilinear edge joinder with top annulus 16 for additional strength and rigidity and to provide a structure so configured that it may be readily formed by molding. The vertical outer surface of neck 19 defines threads 20 to aid in releasably fastening the top member and somewhat thickened annular ledge 21 about its lower portion to abut against a similar structure provided by the top member to form somewhat of a seal between top and body and to provide additional strength and rigidity in this area.

The peripheral elements defining body 10 are relatively thin and thusly define containment chamber 22 within the body. This chamber, when the body be oriented in normal upright position as illustrated, will contain fluidic attractant against gravity displacement.

Top 11 provides vertical cylindrical side portion 23 defining a skirt that extends downwardly from structural communication with convexly configured top portion 24. The inner surface of side 23 is sized to fit immediately outwardly adjacent the outer surface of cylindrical neck 19 of the body and defines internal threads 25 adapted to operatively engage threads 20 carried by that cylindrical neck. The lower surface of side 23 defines annulus 26 with horizontal lower surface somewhat diametrically larger than the side 23 to provide additional edge strength and a surface against which annular ledge 21 of the neck may fit to form somewhat of a seal between the top and body elements.

Figure 3:
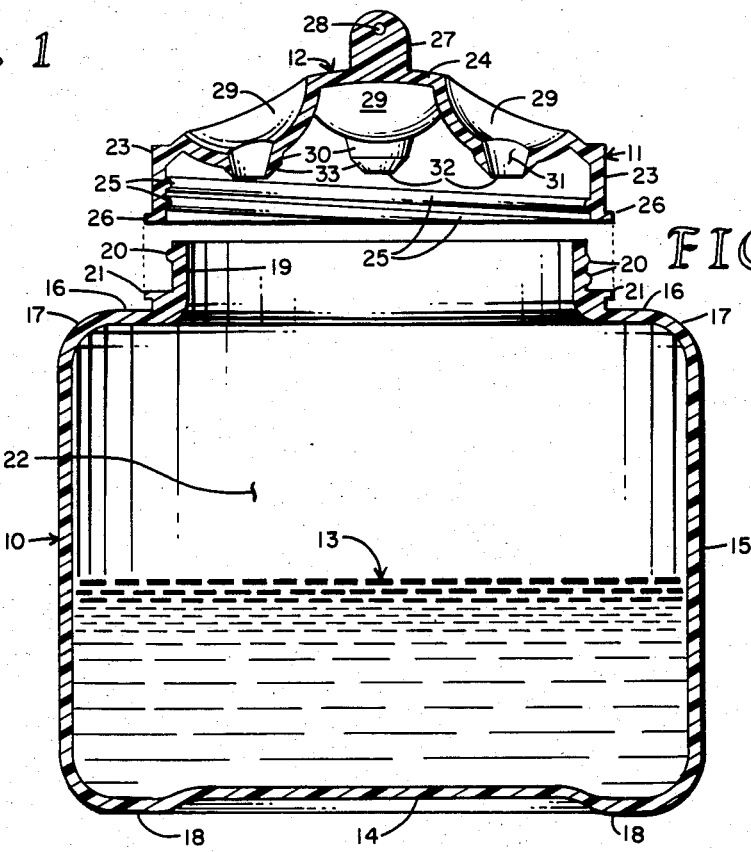
FIG. 3 is a vertical cross-sectional view taken on a diameter of the fly trap of FIG. 1, as on the line 3—3 thereon in the direction indicated by the arrows, with the top member unscrewed to better show the details of the structures.

Upper convex portion 24 of the top provides medially positioned, upwardly extending fastening element 27 defining hole 28 in its upper part to aid the fastening of the element to some hanging type support. Convex portion 24 defines plural concave entry dimples 29 supporting downwardly extending entryway tubes 30 in their medial portions. Each entry dimple is defined by a surface that is a sector of an oblate spheroid. The size and positioning of dimples is not particularly critical, so long as the dimples be sized so that a reasonable number may be defined in a spaced relation in convex portion 24 of the top. An entryway tube 30 extends from the medial portion of each dimple, to a spaced distance therebelow, but generally not such a great distance that it extends vertically below the top of the trap body. Each entryway tube defines a medial channel 31 shaped as a truncated cylindrical cone with its apex vertically lowermost. Entryway channel size is somewhat critical in that throughout the entryway's length it must be of sufficient areal size to allow the passage of a crawling fly, but yet the bottom portion of the channel must be small enough that it will not readily allow the upwardly passage of a flying fly. That is, the entryway tube's lower orifice should have a diameter somewhat less than the length of the wing span of an average fly to be entrapped. This structure prevents a fly in the entrapment chamber from exiting therefrom by flying upwardly through the entryway channels. Lowermost edge 32, defining the lower orifice of each entryway, is sharply acute, as illustrated, being formed by cone 33 of somewhat larger central angle defining the outer peripheral portion of the lowermost part of each entryway 32, as illustrated particularly in the cross-section of FIG. 3.

Body 10 is formed from some material that is translucent to light and heat waves. The material must also be sufficiently rigid to fulfill its purpose and must not be particularly reactive with aqueous based fermenting solutions to be contained thereby. Glass and many plastics fulfill these conditions admirably. The body is preferably not colored.

Top 11 is formed of some optically opaque material that is not translucent to light. The light opaqueness of the top and light translucency of the body are necessary to the proper functioning of my invention, as this causes flies coming to the upper orifice of entryway channel 31 to tend to move downwardly therethrough since they see stronger light therebelow then therein and tend to move much more readily toward lighter areas then toward darker areas. This same lighting condition also causes a fly partially within the entryway to tend to move downwardly therethrough. The top is green-yellow colored so that light reflected therefrom is in the bright yellow band of the spectrum as these colors are an optical attractant to most, if not all, species of flies. The color range in physical terms varies from about 5200 to 5900 Angstroms, in original Munsell terms from 5.0YG 6/10 to 5Y $\frac{5}{8}$, and in artists' terms from thalo yellow-green to cadmium yellow medium. This color will aid in causing flies in the neighborhood of the trap to move closer to the top wherein entryways are defined so that they may there sense the olfactory attractant.

Both top and body structures are configured with reasonably curvilinear shapes to allow formation by molding from plastic material and yet provide a structure that is reasonably thin and lightweight but yet of appropriate strength and durability and one without undue cracking or other physical detrioration common to many plastic products.

Liquid attractant 13 will commonly be carried within the containment chamber defined in body 10. Various substances have heretofore become known as attractants to flies. Most such substances are centered around some sort of an olfactory or sex attractant or an odoriferous organic product particularly of a putrefying nature. Most known attractants are more or less useful and operative with my fly trap.

I have found, however, that an actively fermenting, aqueous based mixture of yeast, egg and milk is especially attractive to flies, safe, convenient and inexpensive of use, and provides an olfactory attractant of such nature as to pass readily from my trap to its environs. Aqueous based mixtures embodying most any amounts of these components, with or without additives, are generally effective, but I have found most effective such mixtures within the following component ranges (by weight):

Yeast: $\frac{1}{2}$% to 5%
Egg (liquid): 5% to 25%
Milk (solids): 1% to 20%
Water: 50% to 4%

The yeast may be any of the common types of brewers' or bakers' yeast, but preferably will have an aerobic fermentative type action, though it seems not to make too much difference if the yeast reacts in an organic cycle. The yeast product that has been used in experimentation with the foregoing formulas was Fleischmann's DIRECT dry powdered yeast as manufactured by Nabisco Brands, Inc., of East Hanover, N.J. 07936. The egg may be presented in the form of fresh chicken egg or its components, or various other types of eggs or egg solids, so long as it presents protein and carbohydrate material that may aid the fermentation process. The egg material used in the experimentation determining the foregoing formulas was dried whole egg solids (containing less than 2% silico aluminate) produced by Commercial Creamery Co., of Spokane, Wash. The milk may be presented in liquid or solid form or any of the various stages therebetween, and may contain all milk components or selected ones, again so long as there be protein and carbohydrate material therefrom to aid the fermentation reaction. The milk product used in the foregoing formulations was pasteurized, extra grade, spray process, non-fat dry milk as produced by Darigold Farms of Spokane, Wash.

Often the fermentation action of my attractant may be greater than necessary to fulfill its purpose, especially in warmer climates and areas with warm nights. In such situations, small amounts of sodium bicarbonate may be added to the attractant to retard the fermentation process and give longer attractant life. Sodium bicarbonate, in the form of ordinary commercial baking soda, may be added to the attractant mixture in amounts up to 0.1%, the exact amount depending upon the required degree of retardation. An addition of 0.05% is preferred.

For most convenience, my attractant may be prepared in a dry powdered form and merchandised in predetermined qauntities in such form to be thereafter admixed with a predetermined amount of water by an ultimate user for use in my trap.

Having thusly described the structure of my trap and the nature of its attractant, their use and function may now be understood.

To use my invention, firstly a trap is constructed according to the foregoing specification. The top is removed and the containment chamber partially filled with an aqueous attractant of the type described. The top is then replaced and the trap established and supported in an area where flies are to be entrapped, preferably an outdoor area of temperature ranging above 50 degrees fahrenheit and with a reasonable amount of light. Under such conditions the attractant mixture will, in due course, commence fermentation.

As fermentation occurs, the gaseous and olfactory products thereof will pass from the aqueous media into the containment chamber and ultimately upwardly through the entryway channels to the ambient atmosphere about the trap. This passage of the olfactory products of fermentation will occur largely by diffusion, though possibly also to some degree by reason of gaseous pressure generated within the containment chamber by the fermentive process itself.

It is to be noted that the gaseous fermentative products, and other particulated olfactory products that may not be gaseous, will tend to congregate to some degree in the dimple structures about the entryways, firstly, because they are generally heavier than the ambient atmosphere thereabout and, secondly, because of the configuration of the dimples, diffusion will be greater therein and immediately adjacent the external orifice of the entryways. The olfactory attractant will then form somewhat of a bulbous distribution about each entryway with concentration inversely proportional to distance therefrom. A fly sensing this attractant will generally tend to move toward its strongest point of concentration and thus ultimately to the external orifice of an entryway.

The color of the top tends to cause flies to move to the neighborhood of a trap because of the optical attraction of flies thereto. As this occurs, normally the flies will be brought within the range of the olfactory attractants and thence influenced thereby.

Though flies are not a particularly social insect, they do tend to congregate in the vicinity of other flies apparently because they associate the congregation of their brethren with the presence of some desirable condition and especially food. It is to be noted that with the translucent or transparent body defining the entrapment chamber, a fly external of that chamber will generally be able to see other flies therein and will be attracted to the environs of the trap again by reason of this condition. This is especially true of flies, as distinguished from other insects, because their vision is generally more acute.

As a fly comes into the range of and is influenced by the olfactory attractant generated in the entrapment chamber, it will move toward the point of highest concentration which generally will be the external orifice of one of the entryways 30. When a fly gets to this position, the attractant will be even more concentrated in the entryway channel. The fly will also, by reason of its natural instincts, tend to approach the entryway channel since it tends to move from an upward position downwardly in its normal course of travel, especially when in search of food. As the fly approaches the external orifice of the entryway channel, it will tend firstly to move toward that orifice since the concentration of olfactory attractant is greater in that area. Since the concentration tends to increase in the entryway channel as that channel extends downwardly into the entrapment chamber, the fly will tend to move downwardly through the entryway channel, either by flying or crawling. This motion is enhanced again not only by the natural instinct of a fly to move downwardly but also its instinct to move toward a light source. In this regard it is to be noted that the material from which the entryway channel is defined is opaque, and since the fly is approaching from an upward position, the area of most light as viewed by the fly, will be downwardly below the entryway channel, since light enters the entrapment chamber through the walls defining it.

As the fly moves downwardly through the entryway channel, it will come to the lower orifice thereof exiting into the entrapment chamber. Since there is stronger light therebelow, the fly will enter the entrapment chamber and thence fly thereabout. Normally, in this position, the fly could not exit from the entry channel, in any event. Once in the chamber the fly most probably cannot exit upwardly through an entryway channel by flying because its average wing span is greater than the diameter of the entryway orifice. The fly generally has no place to alight immediately adjacent the internal orifice of an entryway, or in fact elsewhere, because of the configuration of the structures and their substantially vertical walls. These walls also are of a smooth nature which gives little if any footing to allow a fly to alight or crawl thereabout.

A fly in the containment chamber will be dissuaded by its instincts from attempting to crawl back upwardly through an entry orifice because of the sharp lower edge defining the lower orifice of the entry tube, if in fact it be physically possible to do so. A fly's natural instinct is not to crawl over a sharp edge. All of these features then tend to substantially increase the probability of a fly's remaining within the entrapment chamber once it enters therein and to substantially decrease the probability of its exiting therefrom through one of the entryways.

Once entrapped within the entrapment chamber, a fly normally will become alarmed, frightened and confused and by reason of this it will expend more energy than it normally would. By reason of this energy expenditure, its ultimate demise is hastened and normally it will tire of flying and come to rest on the surface of the fluid attractant and ultimately drown.

It is to be further noted that once an insect is in the entrapment chamber, its demise will also be aided by the greenhouse effect in that chamber which will tend to cause heat rays entering into the chamber to be reflected from the inner surface thereof and remain within the chamber to increase the temperature therein. This increased temperature will tend to enhance fly activity, cause more rapid exhaustion and aid ultimate asphyxiation. If the yeast in the chamber causes an aerobic type fermentative reaction, a major product of metabolism will be carbon dioxide and this also will tend to asphyxiate any flies in the chamber, since they are oxygen breathing insects.

As flies die in the entrapment chamber, their bodies will congregate in the aqueous solution therein and those bodies tend to add further nutrient material to aid the fermentation and putrefaction processes within the entrapment chamber to generate more olfactory attractants for other flies yet to enter that chamber. When the chamber becomes too congested with fly bodies and debris or its fermentation process is exhausted, the top of the trap may be removed, the contents of the entrapment chamber disposed of and new attractant established therein for use again in the same cycle as aforedescribed.

From the foregoing description it is to be particularly noted that the various features of my trap tend to enhance fly capture and ultimate demise by relating those various trap features to the instinctual behavior or "psychology" of the fly. By reason of this relationship, the potentiality of entrapment of flies is substantially increased over traps not embodying the features and the combination of all features substantially enhances the probability of fly entrapment over other known fly traps.

The foregoing description of my invention is necessarily of a detailed nature so that a specific embodiment of it might be set forth as required, but it is to be understood that various modifications of detail, rearrangement and multiplication of parts might be resorted to without departing from its spirit, essence or scope.

Having thusly desribed my invention, what I desire to protect by Letters Patent, and

What I claim is:

1. A containment type fly trap comprising in combination:
    a peripherally defined body having a neck in its upper portion with means to releasably interconnect a top, said body defining an entrapment chamber and being translucent to light and heat waves and
    a top having a lower cylindrical portion configured to fit about and releasably interconnect with the body neck and an upwardly convex top element defining
        a plurality of spacedly arrayed concave entryway dimples, each carrying in the medial portion thereof a downwardly extending entryway tube, each said entryway tube defining an entryway channel to allow downward entry of flies therethrough to the entrapment chamber and means to aid in preventing flies' upward exit from the entrapment chamber through the entryway channels.

2. The invention of claim 1 further characterized by:
    the top being formed of light opaque, bright colored material of color in the range from yellow-green to yellow 3. The invention of claim 1 further characterized by:
    each entryway having a smooth external surface, a size slightly less than the average wing span of flies to be entrapped and a sharp edge defining its lowermost orifice.

4. The invention of claim 1 carrying a fluidic attractant, filling a part of the entrapment chamber, comprising, in percentage by weight:
    yeast: ½% to 5%
    egg: 1% to 25%
    milk solids: 1% to 20%
    water: 50% to 4%

5. The invention of claim 4 further including up to 0.1 percent by weight of sodium bicarbonate as a retardant to excessive fermentative action.

6. A containment type fly trap comprising in combination:
    a body member having in its upper part a peripherally defined cylindrical neck defining external threads to releasably interconnect a top, said body being formed of material translucent to light and heat waves and defining an internal entrapment chamber communicating to the channel defined by said neck; and
    a top member having a lower cylindrical neck portion, defining internal threads to threadedly engage the neck of the body, and an upper convex top portion to cover the channel defined by said neck, said convex top portion being formed of light opaque bright yellow to yellow-green material and
    having a plurality of spaced concave entryway dimples, each dimple, carrying in a medial position an entryway tube extending downwardly no further than the lowermost surface of the cylindrical neck portion, each entryway tube
    having a smooth external surface, being configured as a truncated cylinder with apex lowermost, and defining a medial entry channel having a sharp lower orifice.

7. In a top entry, containment type fly trap having a containment chamber peripherally defined by a body formed of material at least translucent to light and heat waves, the invention comprising:
    a top covering an orifice defined in the upper portion of the associated body, said top
    being formed of material opaque to light waves,
    having a color in the range from yellow to yellow-green,
    having a plurality of spaced concave entry dimples, each carrying
    a medially positioned, downwardly extending entryway tube having a smooth external surface and a size slightly smaller than the average wingspan of flies to be trapped, each said entryway tube
    extending downwardly a spaced distance from the top and into the associated containment chamber.

* * * * *